United States Patent [19]
Henrick

[11] 4,024,278
[45] May 17, 1977

[54] MITE CONTROL USING ALKYL ESTERS OF ALKYNYL ACIDS

[75] Inventor: Clive A. Henrick, Palo Alto, Calif.

[73] Assignee: Zoecon Corporation, Palo Alto, Calif.

[22] Filed: Aug. 25, 1975

[21] Appl. No.: 607,538

Related U.S. Application Data

[60] Division of Ser. No. 535,611, Dec. 23, 1974, abandoned, which is a continuation-in-part of Ser. No. 355,846, April 30, 1973, abandoned.

[52] U.S. Cl. .............................. 424/314; 424/312; 424/313

[51] Int. Cl.² .......................................... A01N 9/24
[58] Field of Search ............................ 424/312, 314

[56] References Cited

UNITED STATES PATENTS

| | | | |
|---|---|---|---|
| 3,619,165 | 11/1971 | Covey | 71/70 |
| 3,867,415 | 2/1975 | Chodnekar et al. | 424/312 |

*Primary Examiner*—V. D. Turner
*Attorney, Agent, or Firm*—Donald W. Erickson

[57] ABSTRACT

Esters of alkynyl alcohols or alkynyl acids are useful for the control of mites.

7 Claims, No Drawings

MITE CONTROL USING ALKYL ESTERS OF ALKYNYL ACIDS

This is a division of Ser. No. 535,611, filed Dec. 23, 1974, now abandoned, which is a continuation-in-part of Ser. No. 355,846, filed Apr. 30, 1973, now abandoned.

This invention relates to the use of esters of alkynyl alcohols or alkynyl acids for the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and due to their wide distribution attack a variety of plants and trees. Spider mites of the family Tetranychidae, such as *Tetranychus urticae, Tetranychus canandensis, Tetranychus cinnabarinus, Tetranychus pacificus, Bryobia praetiosa, Oligonychus pratensis, Oligonychus ilicis, Panonychus citri, Panonychus ulmi*, and similar related species, are of particular biological interest and economic importance. Other mites are those of the family Tarsonemidae, such as *Steneotarsonemus pallidus*.

Compounds of the present invention of the following formulas I, II and III are control agents for mites.

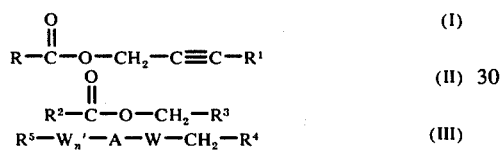

wherein,

R is an aliphatic hydrocarbon group of eleven to thirty carbon atoms;

$R^1$ is hydrogen, alkyl of one to seven carbon atoms, chloro or chloroalkyl of one to seven carbon atoms; $R^2$ is aliphatic alkynyl of two to twenty carbon atoms or chloro aliphatic alkynyl;

$R^3$ is hydrogen, alkyl, alkenyl, alkynyl, cycloalkyl, or aryl; with the proviso that the total number of carbon atoms in the groups $R^2$ and $R^3$ is at least eleven;

A is arylene or cycloalkylene;

W is

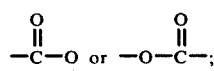

W' is

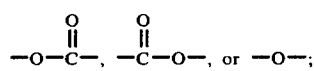

n is zero or one;

$R^4$ is lower alkynyl or lower chloroalkynyl; and $R^5$ is hydrogen, lower alkyl, lower alkenyl, lower alkynyl, lower chloroalkynyl, halo or nitro.

The compounds of Formulas I, II, and III are effective miticides having particularly good ovicidal and larvicidal activity. A compound of formula I, II, or III, or mixtures thereof, can be applied at dosage levels of the order of 0.001 to 1%. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound is employed, although higher concentrations of the active compound can be used depending on the type of application and effectiveness of the active ingredient.

The compounds of Formula I can be prepared from the corresponding acids (RCOOH) and the alcohol

by esterification under acidic conditions or from the acid chloride RCOCl and the alcohol

in the presence of an HCl acceptor.

Alternatively, the esters of Formula I can be prepared by reacting a metal e.g. sodium, salt (RCOO Metal) with an alkynyl bromide of the formula

The compounds of formula II can be prepared from the corresponding acid

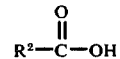

and the alcohol $R^3$—$CH_2OH$ by esterification under acidic conditions or from the acid chloride

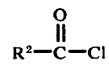

and the alcohol $R^3$—$CH_2OH$ in the presence of an HCl acceptor.

The compounds of Formula III wherein

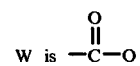

and

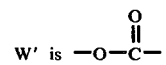

or —O— when n is one can be prepared from the corresponding acid

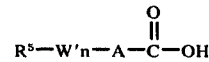

and the alcohol $R^5CH_2OH$ by esterification under acidic conditions or from the acid chloride

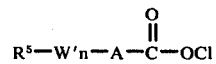

and the alcohol $R^5CH_2OH$ in the presence of an HCl acceptor.

Similarly, the compounds of Formula III wherein

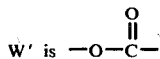

and

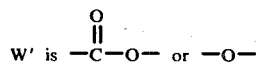

when n is one can be prepared from the corresponding acid R⁵—COOH or acid chloride thereof and the alcohol HO—A—OH or R⁵—W'n—A—OH.

The term "aliphatic hydrocarbon group", as used herein, refers to a straight or branched chain hydrocarbon chain containing 11 to 30 carbon atoms and optionally containing one to two sites of olefinic unsaturation or one or two sites of acetylenic unsaturation.

The term "alkyl", as used herein refers to a straight or branched chain saturated hydrocarbon chain containing one to 20 carbon atoms.

The term "aliphatic alkynyl" as used herein refers to a straight or branched chain hydrocarbon group of two to 20 carbon atoms and containing at least one site of acetylenic unsaturation and optionally containing one or two sites of olefinic unsaturation and/or one additional site of acetylenic unsaturation.

The term "alkenyl" as used herein refers to a straight or branched chain hydrocarbon group of two to 20 carbon atoms and containing one or two sites of olefinic unsaturation.

The term "alkynyl" as used herein refers to a straight or branched chain hydrocarbon group of two to 20 carbon atoms and containing one or two sites of acetylenic unsaturation.

The term "chloroalkynyl" as used herein refers to a chloro-substituted alkynyl group.

The term "cycloalkyl" as used herein refers to a cyclic alkylene group of four to six carbon atoms optionally substituted by one or two alkyl or alkoxy groups.

The term "aryl" as used herein refers to a phenyl or naphthyl group optionally substituted by one or two alkyl, alkoxy, chloro or nitro groups.

The term "lower alkynyl" as used herein refers to an alkynyl group of two to eight carbon atoms.

The term "lower chloroalkynyl" as used herein refers to a chloro-substituted lower alkynyl group.

The term "lower alkenyl" as used herein refers to an alkenyl group of two to eight carbon atoms.

The term "lower alkyl" as used herein refers to an alkyl group of one to eight carbon atoms.

The following examples are provided to illustrate the synthesis and activity as miticides of the esters of the present invention. Temperature is given in degrees Centigrade. All boiling points were measured by short-path distillation.

EXAMPLE 1

To a solution of 3.00 g. (13.5 mmoles) of tetradecanoic acid in 40 ml. of dry ether at 0° is added 1.42 ml. (19.74 mmoles) of thionyl chloride and 0.2 ml. (2.63 mmoles) of dimethylformamide. The solution is allowed to warm to room temperature and then is stirred for 2½ hours. The solvent is removed from the top layer of the now biphasic mixture by evaporation and the residue is taken up in 30 ml. of ether. To this solution a 0° under nitrogen is added 1.15 ml. (19.75 mmoles) of propargyl alcohol and 2.1 ml. (2.0 mmoles) of pyridine. The reaction mixture is allowed to warm to room temperature and stirred for 1 day, ether and water are then added, the organic phase separated, the aqueous phase extracted with ether, and the combined organic phases washed with 3N sulfuric acid, 10% aqueous sodium carbonate, water, saturated aqueous copper sulfate, water and brine. The reaction mixture is dried over calcium sulfate and concentrated to yield propargyl tetradecanoate, boiling at 125° at 0.25 mm.

Typical compounds prepared by the above procedure are shown in the following table.

CHEMICAL

Propargyl 3,7,11-trimethyltrideca-2,4-dienoate b.p. 100° at 0.01 mm
Propargyl hexadecanoate b.p. 121° at 0.08 mm
Propargyl 3,7,11-trimethyldodeca-2,4-dienoate
Propargyl dodecanoate b.p. 90° at 0.1 mm
2-Butynyl 3,7,11-trimethyldodeca-2,4-dienoate
2-Butynyl dodecanoate

EXAMPLE 2

To a mixture of 130 g. 2-butyne-1,4-diol, 150 ml. anhydrous benzene, and 134 ml. anhydrous pyridine is added, at 10°–20°, 125 ml. of thionyl chloride over a period of 6 hours. The mixture is kept at room temperature overnight and then is poured into 1 liter of ice with stirring until the ice is melted. The aqueous phase is separated and extracted with ether (4 × 120 ml.). The combined organic layers are washed in turn with saturated aqueous sodium bicarbonate (2 × 70 ml.) and saturated aqueous sodium chloride (1 × 50 ml.) and then is dried over calcium sulfate. The mixture is fractionally distilled to yield 52 ml. of 4-chloro-2-butyn-1-ol, b.p. 110°–114° at 23 mm.

EXAMPLE 3

To a mixture of 1.04 g. of 4-chloro-2-butyn-1-ol prepared in Example 2, 40 ml. anhydrous ether, and 1.64 g. of dodecanoyl chloride at 0° under argon is added 1.1 ml anhydrous pyridine. The mixture is allowed to warm to room temperature and then is stirred for 2 days. The reaction mixture is worked up using the procedure of Example 1 to yield 1.1 ml. of 4'-chloro-2'-butyn-1'-yl dodecanoate, b.p. 114°–116° at 0.03 mm.

Following the procedure of Example 3, 4-chloro-2-butyn-1-ol is reacted with each of hexadecanoyl chloride, tetradecanoyl chloride, and 3,7,11-trimethyl-2,4-dodecadienoyl chloride to yield 4'-chloro-2'-butyn-1'-yl hexadecanoate
4'-chloro-2'-butyn-1'-yl tetradecanoate
4'-chloro-2'-butyn-1'-yl 3,7,11-trimethyl-2,4-dodecadienoate

EXAMPLE 4

A mixture of 3.0 g. propynoic acid, 7.26 g. of hexadecanol, 30 ml. anhydrous benzene, and 0.2 g. p-toluenesulfonic acid is boiled for 1.5 hours. Ether (150 ml.) is added and the mixture is washed in turn with 15% aqueous sodium bicarbonate (2 × 50 ml.), water (1 × 50 ml.), and saturated aqueous sodium chloride (1 × 50 ml.) and then is dried over calcium sulfate. The solvent is removed by rotary evaporation to yield 9.1 g. of crystalline product which is recrystallized from a mixture of pentane and methanol to yield 2.49 g. of white crystalline hexadecyl propynoate, m.p. 36°.

Following the procedure of Example 4, each of tetradecanol, dodecanol, 9-octadecenol and 4-phenylbenzyl alcohol is reacted with propynoic acid to yield
tetradecyl propynoate
dodecyl propynoate
9-octadecenyl propynoate
4-phenylbenzyl propynoate

EXAMPLE 5

A mixture of 2.0 g. of 2-butynoic acid, 4.02 g. of hexadecanol, 20 ml. of anhydrous benzene and 0.2 g. p-toluenesulfonic acid monohydrate is boiled for 3 hours and the reaction mixture is worked up as in Example 4. The product is purified by distillation to yield 2.4 ml. of hexadecyl 2-butynoate, b.p. 145°–152° at 0.03 mm.

Following the procedure of Example 5, each of pentadecanol, tetradecanol, tridecanol, dodecanol, 9-octadecenol, 4-ethyl cyclohexylmethanol is reacted with 2-butynoic acid to yield
pentadecyl butynoate
tetradecyl butynoate
tridecyl butynoate
dodecyl butynoate
9-octadecenyl butynoate
4-ethylcyclohexylmethyl butynoate

EXAMPLE 6

To a mixture of 10.15 g. of terephthaloyl chloride, 8.41 g. propargyl alcohol and 200 ml. anhydrous ether at 5° under nitrogen is slowly added with stirring 16.1 ml. of pyridine. The reaction mixture is stirred for 4 hours at 5° and for 2½ hour at room temperature. Water (2 ml.) is added and the mixture is stirred for ½ hour. Additional water (100 ml.) is added, the organic layer is extracted with ether and pentane and the reaction mixture is worked up using the procedure of Example 1 to yield bis(propargyl)terephthalate, m.p. 109–109.5.

Using the procedure of Example 6, each of 2-butyn-1-ol and 4-chloro-2-butyn-1-ol is reacted with terephthaloyl chloride to yield bis(2-butyn-1-yl) terephthalate and bis(4-chloro-2-butyn-1-yl) terephthalate

EXAMPLE 7

A mixture of 8.0 g. of p-hydroxybenzoic acid, 125 ml. dimethylformamide, 13.0 g. of propargyl chloride and 24.0 g. of anhydrous potassium carbonate is heated at 75° for 32 hours and then is allowed to stand at room temperature for 3 days. Ether (150 ml.) pentane (100 ml.) and water (100 ml.) is added, the organic layer is separated and washed in turn with water (2 × 50 ml.) and saturated aqueous sodiumm chloride (1 × 50 ml.) and then is dried over calcium sulfate. Solvent is removed by rotary evaporation to yield propargyl 4-propargyloxybenzoate, m.p. 44.5–45.

Adult mites (*Tetranychus urticae*) were allowed to oviposit for 24 hours on the upperside of lima bean leaf discs (1 cm.) on moist cotton wool. After 24 hours, the adults were removed and the leaf discs were then dipped in acetone solutions of the compound to be tested. After submersion for about 1 second, the solvent on the leaf discs is allowed to evaporate and the leaf discs are then glued to a plastic petri dish to prevent crumpling. 5 days later, the number of unhatched eggs is calculated as a percentage of the total number originally present.

In a second test, adult spider mites (*Tetranychus urticae*) were allowed to oviposit on bean leaves in the confinement of 1.5 cm. circles of tanglefoot glue (mite barrier). Adults were removed after 24 hours. All eggs hatched after 6 days after removal of the adults. Then the leaves were sprayed, until run-off, with the compound to be tested diluted in water with 0.1% Tween 20. The mortality was evaluated 72 hours after spraying.

The results of these tests are presented in Table 1 below:

Table I

| Compound | % eggs unhatched | % cmpd. in soln. | % larvae mortality | % cmpd. in soln. |
| --- | --- | --- | --- | --- |
| Propargyl tetradecanoate | 62 | 0.1 | 81 | 0.1 |
| Propargyl 3,7,11-trimethyl-2,4-tridecadienoate | 25 | 0.1 | 100 | 0.1 |
| Propargyl hexadecanoate | 39 | 0.1 | 97 | 0.1 |
| Propargyl 3,7,11-trimethyl-2,4-dodecadienoate | 89 | 1 | 96 | 0.1 |
| Propargyl dodecanoate | 100 | 1 | 55 | 0.1 |
| 2-Butyn-2-yl 3,7,11-trimethyl-2,4-dodecadienoate | 32 | 0.1 | 100 | 0.1 |
| 4'-chloro-2-'-butyn-1-yl dodecanoate | 85 | 0.1 | 78 | 0.1 |
| Tetradecyl propynoate | 10 | 0.1 | 100 | 0.1 |
| Hexadecyl propynoate | 100 | 0.1 | 100 | 0.1 |
| Hexadecyl 2-butynoate | 84 | 0.1 | 100 | 0.1 |
| Bis(propargyl)terephthalate | 100 | 0.1 | 58 | 0.1 |
| Bis(2-butynyl)terephthalate | 70 | 0.1 | 65 | 0.1 |
| Propargyl 4-propargyloxybenzoate | 69 | 0.1 | 100 | 0.1 |

I claim as my invention:

1. A method for controlling mites of the family Tetranychidae or the family Tarsonemidae which comprises contacting the mite eggs or larvae with an ovicidally or larvacidally effective amount of a compound of the formula:

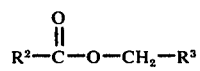

wherein,
$R^2$ is

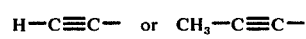

and
$R^3$ is alkyl of 10 to 18 carbon atoms.

2. The method according to claim 1 wherein the compound is hexadecyl propynoate.

3. The method according to claim 1 wherein the compound is hexadecyl 2-butynoate.

4. A method for controlling mites of the family Tetranychidae or the family Tarsonemidae which comprises contacting the mite eggs or larvae with an ovicidally or larvacidally effective amount of 9-octadecenyl propynoate.

5. A method for controlling mites of the family Tetranychidae or the family Tarsonemidae which comprises contacting the mite eggs or larvae with an ovicidally or larvacidally effective amount of 9-octadecenyl 2-butynoate.

6. A method for controlling mites of the family Tetranychidae or the family Tarsonemidae which comprises contacting the mite eggs or larvae with an ovicidally or larvacidally effective amount of 4-phenylbenzyl propynoate.

7. A method for controlling mites of the family Tetranychidae or the family Tarsonemidae which comprises contacting the mite eggs or larvae with an ovicidally or larvacidally effective amount of 4-ethylcyclohexylmethyl 2-butynoate.

* * * * *

UNITED STATES PATENT OFFICE
CERTIFICATE OF CORRECTION

Patent No. 4,024,278  Dated May 17, 1977

Inventor(s) Clive A. Henrick

It is certified that error appears in the above-identified patent and that said Letters Patent are hereby corrected as shown below:

In col. 3, line 3, "W' is $-O-\overset{\overset{O}{\|}}{C}-$" should read -- W is $-O-\overset{\overset{O}{\|}}{C}-$ --.

In col. 3, line 12, "$R^5$-COOH" should read -- $R^4$-COOH --.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*